(12) United States Patent
Starr et al.

(10) Patent No.: US 7,882,656 B2
(45) Date of Patent: Feb. 8, 2011

(54) MANUFACTURED SEED HAVING AN IMPROVED END SEAL

(75) Inventors: Robert A Starr, Auburn, WA (US); Lynn Kenneth Baldwin, Tacoma, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 0 days.

(21) Appl. No.: 12/481,440

(22) Filed: Jun. 9, 2009

(65) Prior Publication Data

US 2009/0320360 A1    Dec. 31, 2009

Related U.S. Application Data

(60) Provisional application No. 61/075,863, filed on Jun. 26, 2008.

(51) Int. Cl.
*A01C 1/06* (2006.01)
(52) U.S. Cl. ........................................ 47/57.6
(58) Field of Classification Search .............. 47/57.6, 47/77
See application file for complete search history.

(56) References Cited

U.S. PATENT DOCUMENTS

| | | | |
|---|---|---|---|
| 5,236,469 A | 8/1993 | Carlson et al. | |
| 5,284,765 A | 2/1994 | Bryan | |
| 5,427,593 A | 6/1995 | Carlson et al. | |
| 5,486,218 A | 1/1996 | Carlson | |
| 5,564,224 A | 10/1996 | Carlson | |
| 5,666,762 A | 9/1997 | Carlson | |
| 5,687,504 A | 11/1997 | Carlson | |
| 5,701,699 A | 12/1997 | Carlson | |
| 6,119,395 A | 9/2000 | Hartle | |
| 6,705,045 B1 | 3/2004 | Francis | |
| 6,888,458 B2 | 5/2005 | Carlson | |
| 7,131,234 B2 | 11/2006 | Carlson | |
| 7,168,205 B2 | 1/2007 | Hartle | |
| 7,207,139 B2 | 4/2007 | McKinnis | |

*Primary Examiner*—Son T. Nguyen
(74) *Attorney, Agent, or Firm*—Christensen O'Connor Johnson Kindness PLLC

(57) ABSTRACT

An artificial seed is provided. The artificial seed includes a seed shell having a live end, a dead end and a perimeter. A nutritive media disposed within the seed shell. The artificial seed also includes a restraint disposed within the seed shell and having a cavity housing an embryo. A primary end seal is attached to the live end of the seed shell. The artificial seed further includes an end seal disposed on the dead end of the seed shell and the end seal has at least three closure axes forming a seal in a direction extending along each one of the closure axes.

9 Claims, 6 Drawing Sheets

MANUFACTURED SEED HAVING AN IMPROVED END SEAL

FIELD OF THE INVENTION

The present disclosure relates generally to artificial seeds and, more particularly, to an improved end seal for an artificial seed.

BACKGROUND OF THE INVENTION

Asexual propagation of plants has been shown for some species to yield large numbers of genetically identical embryos, each having a capacity to develop into a normal plant. Such embryos are usually further cultured under laboratory conditions until they reach an autotrophic "seedling" state characterized by an ability to produce its own food via photosynthesis, resist desiccation, produce roots able to penetrate soil, and fend off soil microorganisms. Some researchers have experimented with the production of artificial seeds, known as manufactured seeds, in which individual plant somatic or zygotic embryos are encapsulated in a seed coat. Examples of such manufactured seeds are disclosed in U.S. Pat. No. 5,701,699, issued to Carlson et al., the disclosure of which is hereby expressly incorporated by reference.

Typical manufactured seeds include a seed shell, synthetic gametophyte and a plant embryo. A manufactured seed that does not include the plant embryo is known in the art as a "seed blank." The seed blank typically is a cylindrical capsule having a closed end and an open end. The closed end is typically sealed by crimping an end of the seed blank to create a dead end seal along a single axis of the seed blank. Thereafter, synthetic gametophyte is inserted into the seed shell and an embryo is sealed within the seed shell by a live end seal.

In the past and as noted above, the dead end seal is formed by crimping an end of the seed shell to close one end of the seed blank. Although such types of dead end seals are successful in closing one end of the seed blank, they are not without their problems. As a non-limiting example, such dead end seals define a seal area that is wider than the outside diameter of the seed blank itself. This creates a need for an oversized guide way when automatically transporting the seed. Further, such dead end seals have a sharp edge that catches and snags on any non-continuous surface. Finally, the flat seal surface acts as a wedge when in close proximity with other seeds to cause a binding effect that disrupts transportation of the seed during manufacture. Thus, there exists a need for an improved dead end seal for an artificial seed.

SUMMARY OF THE CLAIMED EMBODIMENTS

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

An artificial seed is provided. The artificial seed includes a seed shell having a live end, a dead end and a perimeter. A nutritive media disposed within the seed shell. The artificial seed also includes a restraint disposed within the seed shell and having a cavity housing an embryo. A primary end seal is attached to the live end of the seed shell. The artificial seed further includes an end seal disposed on the dead end of the seed shell and the end seal has at least three closure axes forming a seal in a direction extending along each one of the closure axes.

An artificial seed formed in accordance with the various embodiments of the present invention have several advantages over currently available manufactured seeds. In that regard, the end seal provides more seed volume for the storage of nutritive media. Additionally, the end seal maximizes the length of the seed shell profile which provides a more consistent area for pick-up of the seed shell by an automated device during manufacturing of the artificial seed. Also, the end seal defines an outer boundary seal having a diameter that is about the same or less than the diameter of the seed shell itself thereby minimizing the need for oversized transportation guide ways due to the reduced size of the seed shell.

BRIEF DESCRIPTION OF THE DRAWINGS

The foregoing aspects and many of the attendant advantages of this invention will become better understood by reference to the following detailed description, when taken in conjunction with the accompanying drawings, wherein.

DETAILED DESCRIPTION OF THE PREFERRED EMBODIMENT

Figure 1:
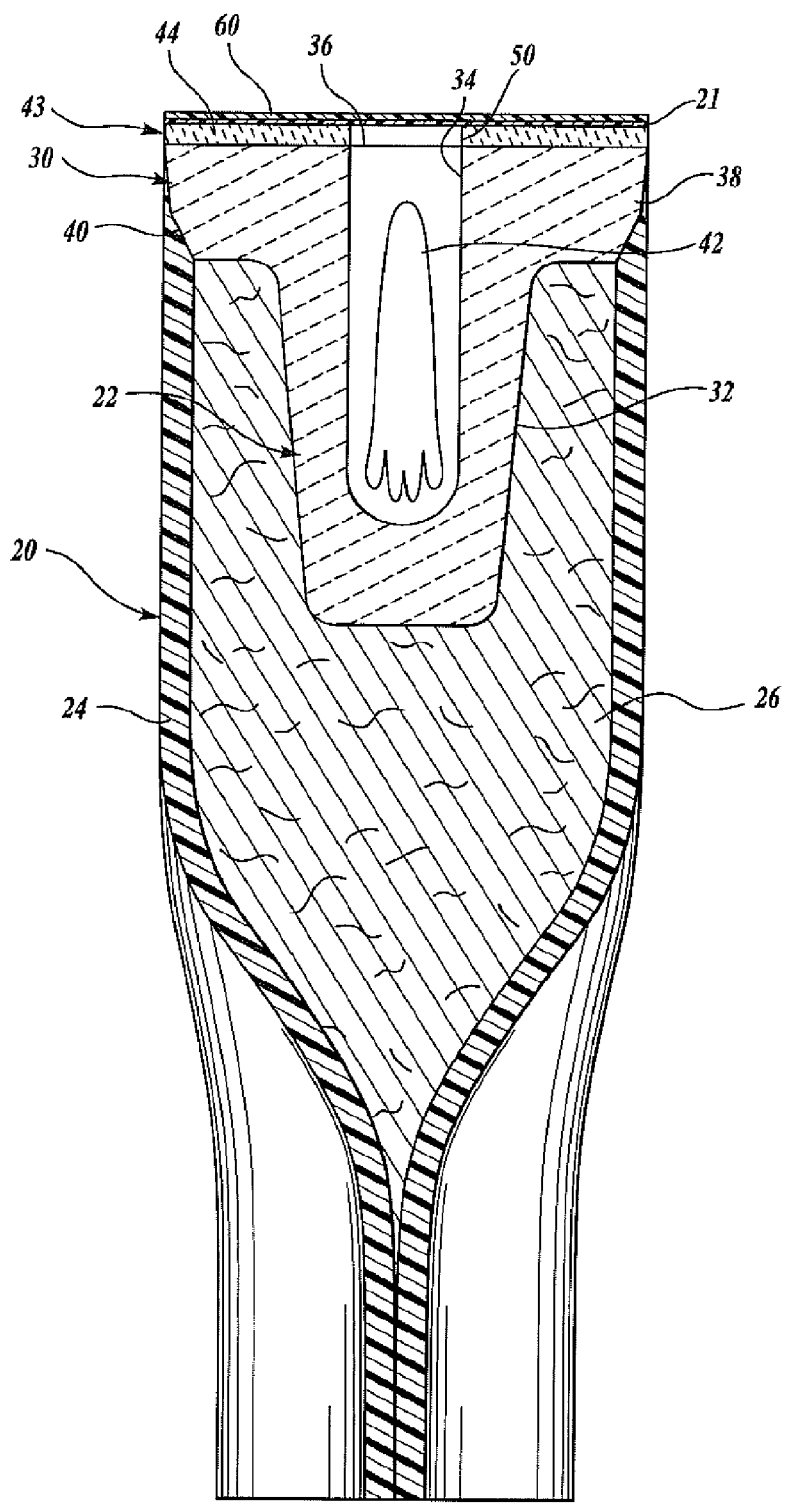
FIG. 1 is a cross-sectional side planar view of an artificial seed having an end seal formed in accordance with one embodiment of the present disclosure.
Figure 2:
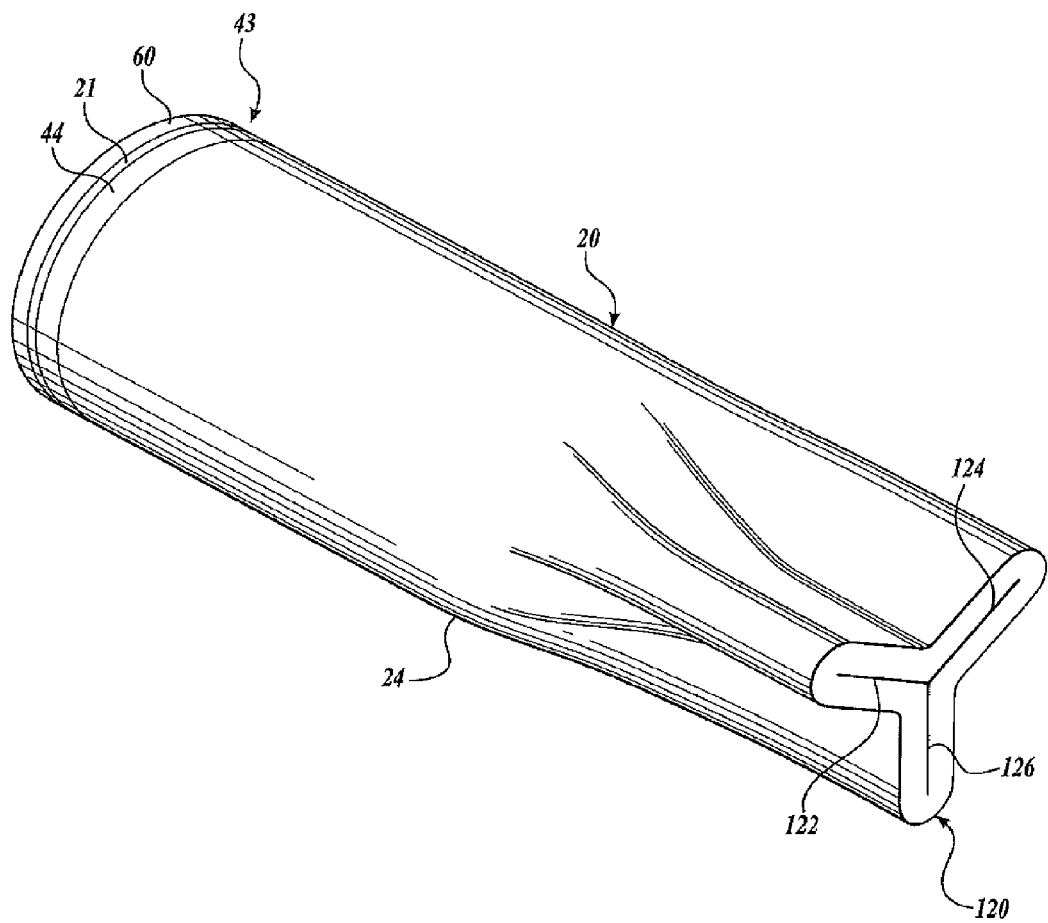
FIG. 2 is an isometric end view of the artificial seed of FIG. 1 showing the end seal.
Figure 3:
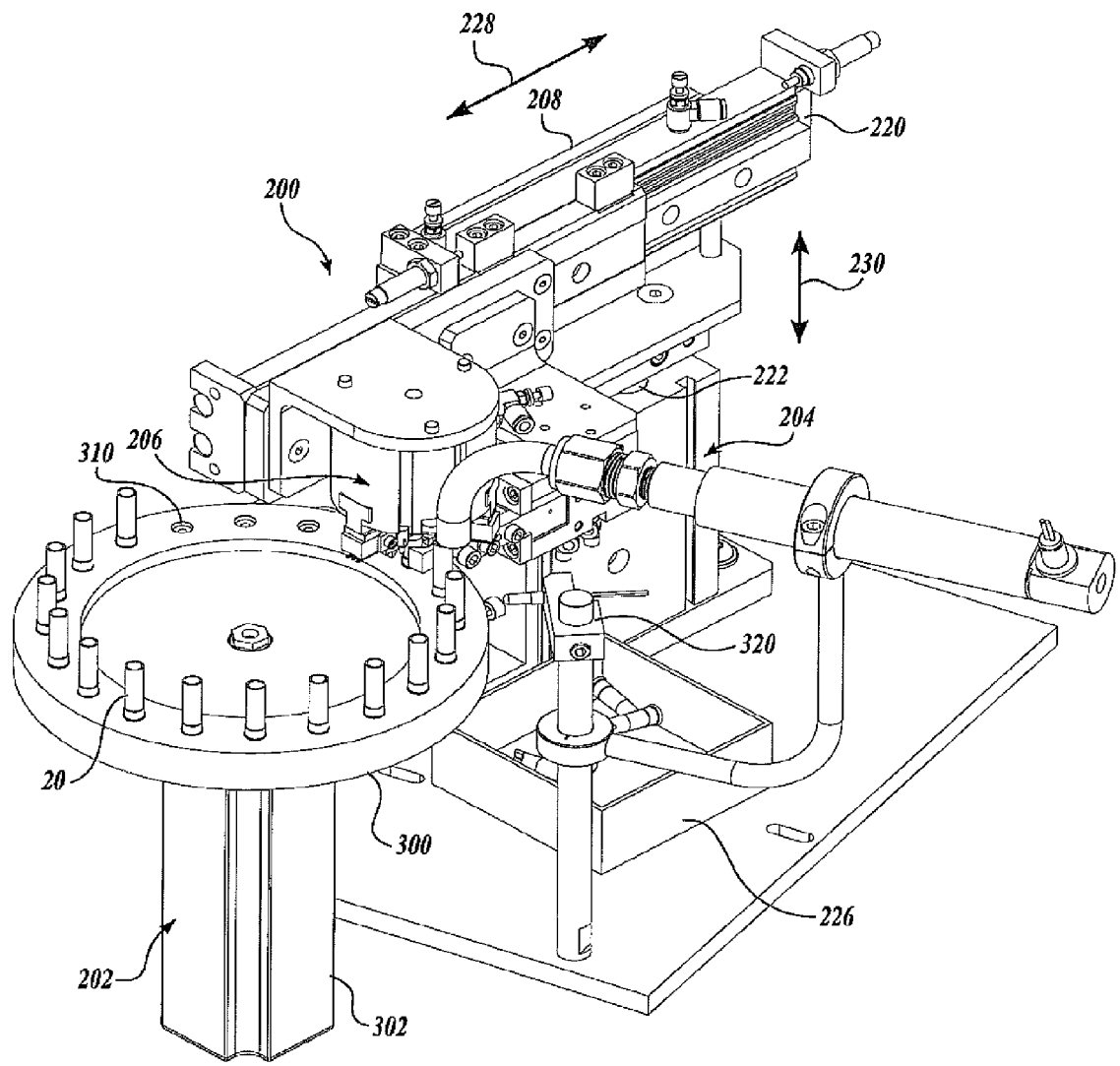
FIG. 3 is an isometric view of one embodiment of an end seal formation assembly used to form the end seal of FIG. 1.

FIG. 1 illustrates an artificial seed 20 having a dead end seal 120 constructed in accordance with one embodiment of the present invention. The artificial seed 20 includes a cylcap 22, a seed shell 24, a nutritive media 26, such as a gametophyte, and the dead end seal 120. The seed shell 24 is suitably formed from a section of tubular material. In one embodiment, the seed shell 24 is a sectioned straw of fibrous material, such as paper. The sections of straw may be pre-treated in a suitable coating material, such as wax.

In other embodiments, the seed shell 24 is formed from a tubular section of biodegradable, plastic material. One such material is a utilized polylatic acid ("PLA") and is sold by NAT-UR of Los Angeles, Calif. Such biodegradable plastic tubes are similarly sectioned into appropriate lengths for a manufactured seed. Further, such biodegradable plastic tubes do not require a wax coating as such tubes are already resistive to environmental elements. It should be apparent that although sectioning tubes is preferred, other embodiments, such as obtaining tubes of appropriate size for use as manufactured seeds, are also within the scope of the present invention.

The cylcap 22, also known as a restraint, is suitably manufactured from a porous material having a hardness strong enough to resist puncture or fracture by a germinating embryo, such as a ceramic or porcelain material, and includes an end seal portion 30 and a cotyledon restraint portion 32. The cotyledon restraint portion 32 is suitably integrally or untarily formed with the end seal portion 30. The cylcap 22 also includes a longitudinally extending cavity 34 extending through the end seal portion 30 and partially through one end of cotyledon restraint portion 32. The open end (or live end) of the cavity 34 is known as a cotyledon restraint opening 36. The cavity 34 is sized to receive a plant embryo 42 therein.

In certain embodiments, as the cylcap 22 is suitably manufactured from a porous material, it may be desirable to coat the cylcap 22 with a barrier material to reduce the rate of water loss and restrict or reduce microbial entry. Such barriers include wax, polyurethane, glaze, nail polish, and a coating sold by Airproducts Airflex 4514.

The end seal portion 30 is suitably circular when viewed in a top planar view and includes sidewalls 38. Although circular is the preferred embodiment of the end seal portion 30, other embodiments and shapes, such as polygonal, square, triangular, oval and other shapes, are also within the scope of the present invention.

In the embodiment of FIG. 1, the sidewalls 38 are defined by the thickness of the end seal portion 30 and has a diameter substantially equal to the inside diameter of the seed shell 24. In certain embodiments, the cylcap 22 is bonded to the seed shell 24 by heat. As a non-limiting example, during manufacturing, the cylcap 22 may be heated to a predetermined temperature, such that when the seed shell 24 and the cylcap 22 are co-joined, heat transferred between the cylcap 22 and the seed shell 24 causes either the seed shell 24, the cylcap 22, or both to melt, thereby bonding the two together. Other methods of bonding the cylcap 22 to the seed shell 24, such as a wax bond or a hot glue melt, are also within the scope of the present invention.

The sidewalls 38 may include a tapered portion 40. The tapered portion 40 may be a chamfer of one end of the end seal portion 30. The tapered portion 40 assists in assembling the cylcap 22 to the seed coat 24 during manufacturing. Although a tapered portion 40 is preferred, other embodiments, such as a cylcap that does not include a tapered portion, are also within the scope of the present invention. An embryo 42 is disposed within the cavity 34 and is suitably sealed therein by a live end seal 43.

The live end seal 43 includes a primary end seal 44 and a secondary end seal 21. The primary end seal 44 is suitably formed from a PLA material described above and includes a centrally located opening 50. The opening 50 is sized to correspond to diameter of the cavity 34 of the cylcap 22 to permit a germinating embryo 42 to pass therethrough. The primary end seal 44 is suitably attached to the end seal portion 30 by a variety of methods, including glue or heat bonding.

As a non-limiting example, the primary end seal 44 is mated to a pre-heated cylcap 22, such that the opening 50 is located above the cavity 34. The heat welds or bonds the primary end seal 44 to the cylcap 22. It should be apparent that the primary end seal 44 may be attached to the cylcap 22 before or after the cylcap 22 is attached to the seed shell 24. Also, if the seed shell 24 is constructed from PLA, it is desirable but not necessary that the melt temperature of the primary end seal 44 and the seed shell 24 be similar.

As another non-limiting example of attaching the primary end seal 44 to the cylcap 22, includes an adhesive gasket. In this example, the primary end seal 44 is heat sealed or bonded to the cylcap 22 with the opening 50 co-axially aligned with the cavity 34. In this process, a form is used to bend edges of the primary end seal 44 around the perimeter of the end seal portion 30 of the cylcap 22. If the melt temperature of the primary end seal 44 and the seed shell 24 are different, then a low bloom cyanoacrylate is used as an adhesive gasket to bond the primary end seat 44 and the seed shell 22.

Heat is applied after the glue and is done so as to thin the glue seal by melting incongruities that typically occur when manufacturing the seed shell 24 and forming the adhesive joint. Thereafter, the cylcap 22, including the primary end seal 44, is attached to the seed shell 24. As noted above, this method is also suitable to a cylcap 22 that is already attached to the seed shell 24. Finally, the foregoing method of attaching a primary end seal 44 to a seed shell 24 may be used for heat weld compatible or incompatible materials.

The secondary end seal 21 will now be described in greater detail. In that regard, the secondary end seal 21 is suitably formed from a well-known sealing material, such as Parafilm®. The secondary end seal 21 is formed and attached to the primary end seal 44 by a well-known method, such as heat bonding or gluing. The secondary end seal 21 also includes a predetermined burst strength to permit a germinating embryo 42 to penetrate through the live end seal 44.

Still referring to FIG. 1, the seed 20 also includes a tertiary seal 60. The tertiary seal 60 and live end seal 43, as used in the present embodiment, define an outer sealing layer and an inner sealing layer, respectively. Although the live end seal 43 has been described as including both a primary end seal 44 and a second end seal 21, it should be apparent that the invention is not intended to be so limited. As a non-limiting example, the live end seal 43 may include only the secondary end seal 21 and, therefore, such embodiments are also within the scope of the present invention.

The combination of the tertiary seal 60 and live end seal 43 creates a seating surface, wherein the sealing layer, defined by the tertiary seal 60, is made from a predetermined material that degrades in structural integrity after a predetermined exposure to environmental conditions. The tertiary seal 60 also serves as an anti-microbial sealant to seal and protect around the embryo as the embryo germinates and emerges from within the seed shell 24 and protects the cotyledon restraint cavity. Suitable materials used to manufacture the tertiary seal 60 include water soluble materials, wax, environmentally degradable materials, and biodegradable materials. Thus, such materials, as well as materials equivalent in structure and properties, are within the scope of the present invention.

The tertiary seal 60 is also suitably manufactured from a hydroxypropylmethylcellulose. Other types of hydrophilic materials and cellulose-based coatings include cellulose acetate phthalate, hydroxypropylethylcellulose, ethylcellulose, methylcellulose, microcrystalline cellulose, and carrageenan. Such materials have the desired properties of having a relatively high structural integrity when dry and such structural integrity degrades when exposed to environmental conditions, such as water.

In certain embodiments, it is desirable to add an anti-microbial agent, such as Thiram 50WP. Any antimicrobial agent that is substantially non-phytotoxic at the desired concentration is also within the scope of the present invention. As is described in greater detail below, a tertiary seal 60 treated with an anti-microbial agent is suitable as a carrier for pesticides to protect the embryo 42 prior to and during germination.

As may be best seen by referring to FIG. 2-6, the dead end seal 120 is formed by an end seal formation assembly 200, as described in greater detail below. The dead end seal 120 includes at least three closure axes indicated by the axis 122-126. Along each respective axis 122-126, a seat is formed during the formation of the dead end seal 120. In the illustrated embodiment, the three closure axes 122-126 are at an obtuse angle relative to each other and are Y-shaped in cross-section. The perimeter ends of the dead end seal 120 define an outer boundary diameter that is less than or equal to the outer perimeter of the seed shell 24. Although it is preferred that the outer boundary diameter is less than or equal to the outer perimeter of the seed shell, it should be apparent that the dead end seal need be so limited. As such, the outer boundary diameter made be greater than the diameter of the seed shell.

Referring now to FIGS. 3-6, the end seal formation assembly 200 includes a carousel 202, a heater assembly 204, and a clamp assembly 206 mounted on a frame 208. The frame 208 includes a slide 220 and riser 222. The well-known slide 220 reciprocates the clamp assembly 206 between the carousel 202 and a storage bin 226 as indicated by an arrow 228. The riser 222 is a known pneumatic or hydraulic lifter adapted to reciprocate the clamp assembly 206 in the direction indicated by the arrow 230. Although described as including both a slide 220 and a riser 222, it should be apparent that the end seal formation assembly 200 is not intended to be so limited. As non-limiting examples, the end seal formation assembly 200 may include either the slider 220 or the riser 222 but not both. Accordingly, such embodiments are also within the scope of the present disclosure.

The carousel 202 includes a tray 300 and a drive mechanism 302. The drive mechanism 302 is a well-known motor, such as a stepper motor. The tray 300 includes a plurality of cavities 310 each sized and configured to receive a seed 20. The plurality of seeds 20 are transitioned into a sensing position where a sensor 320, such as an optical sensor manufactured and sold by Keyence Corp of America of Woodcliff, N.J. 07677 under part number FU-35FZ. In the sensing position, the sensor 320 receives indication of whether a seed 20 is present. If no seed 20 is deemed to be present, the carousel 202 rotates the tray 300 until a seed 20 is indicated as present. Although desirable, the sensor 320 is not necessary for operation of the end seal formation assembly 200.

The heater assembly 204 applies heat to a seed 20 positioned beneath the heater assembly 204. The heater assembly 204 applies a blast of heat onto the seed 20 for a time period sufficient to soften the seed coat 24. Such a time period is a function of the material used to manufacture the seed coat 24 and is derivable by one of ordinary skill in the art As a non-limiting example, the heat assembly 204 applies heat to the seed 20 for approximately 2-4 seconds.

Figure 4:
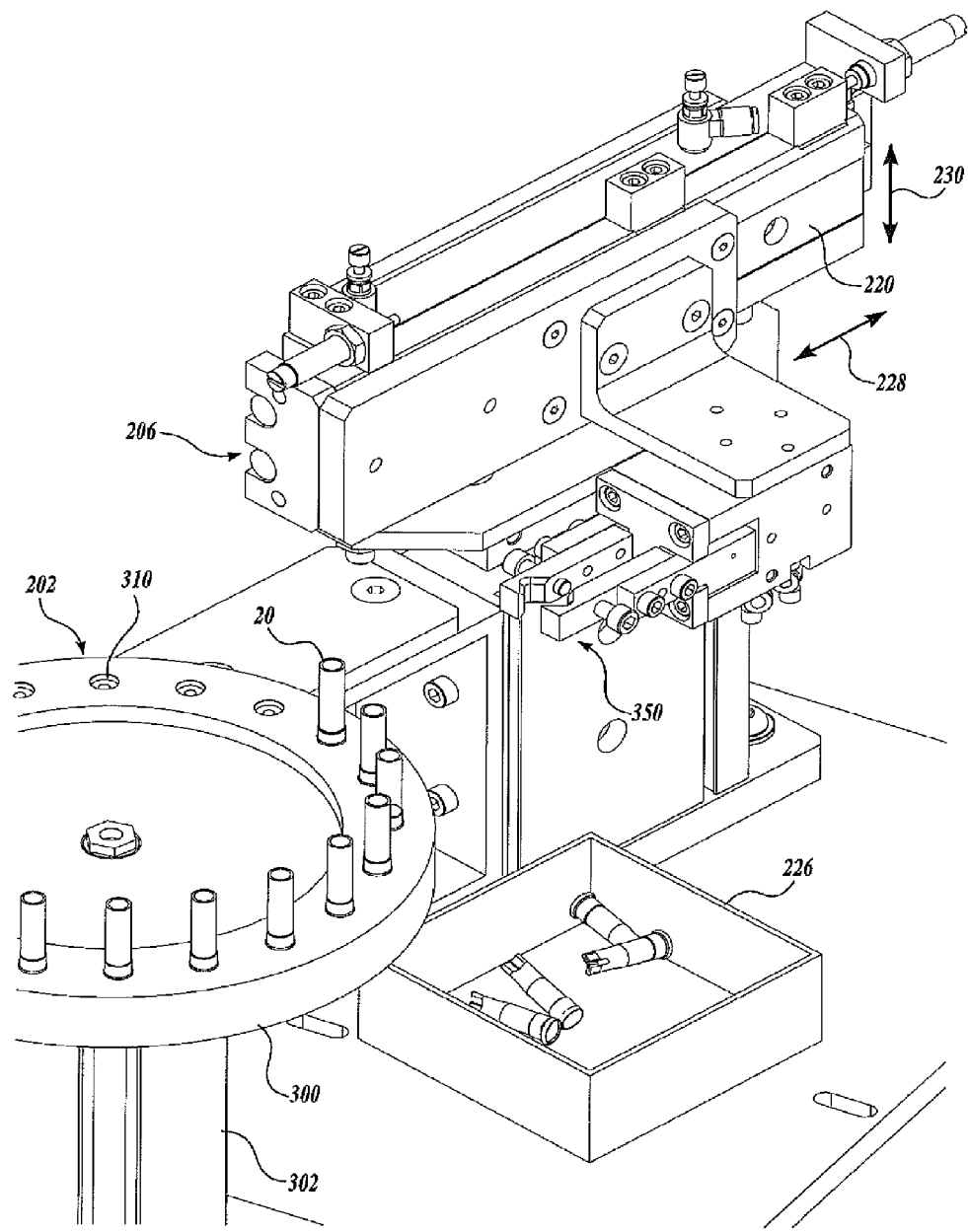
FIG. 4 is an isometric view of the end seal formation assembly of FIG. 3, showing a portion thereof removed for clarity.
Figure 5:
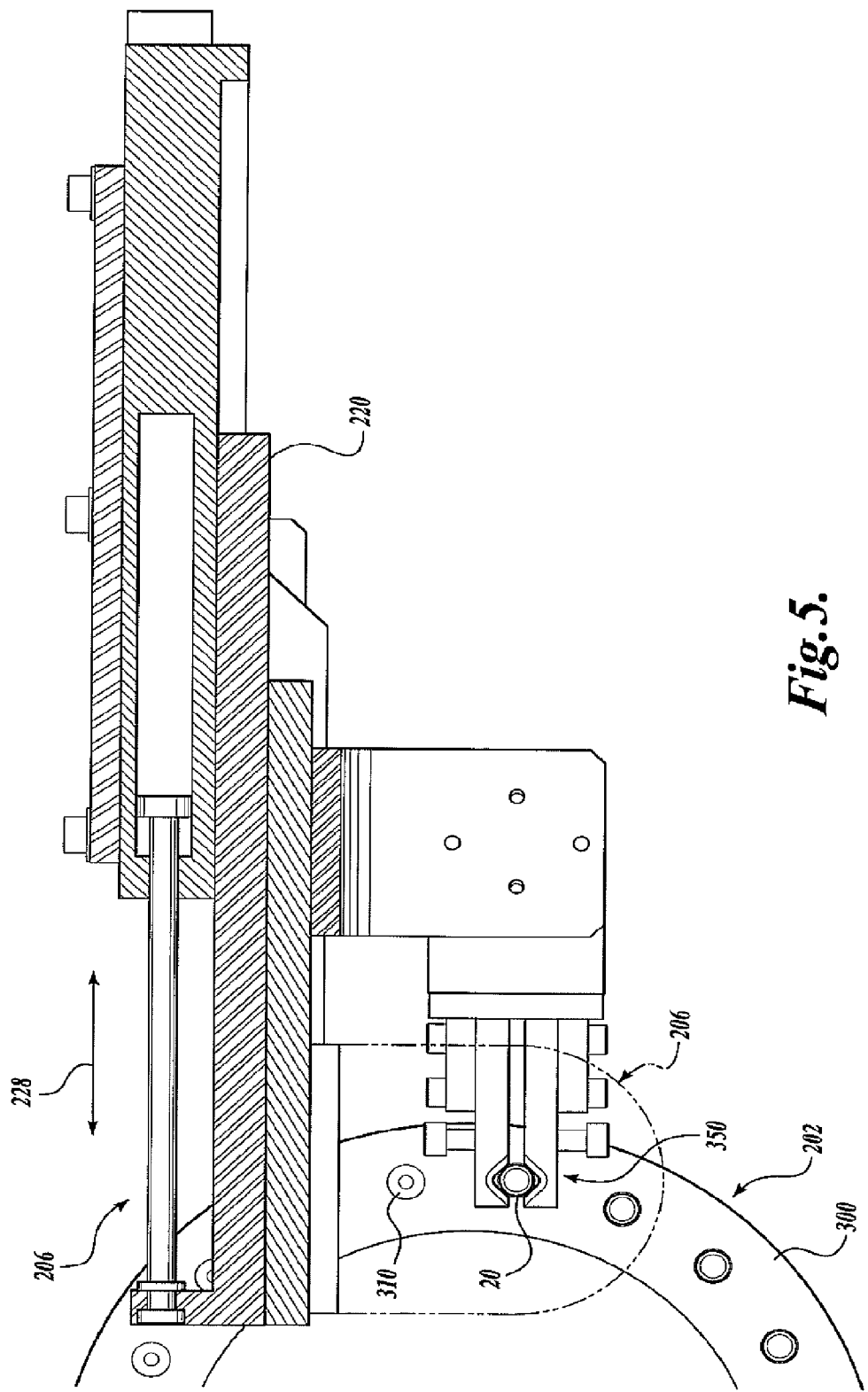
FIG. 5 is a top planar view of the end seal formation assembly of FIG. 4 with portions removed for clarity and showing a seed clamp of the end seal formation assembly clamping an artificial seed.
Figure 6:
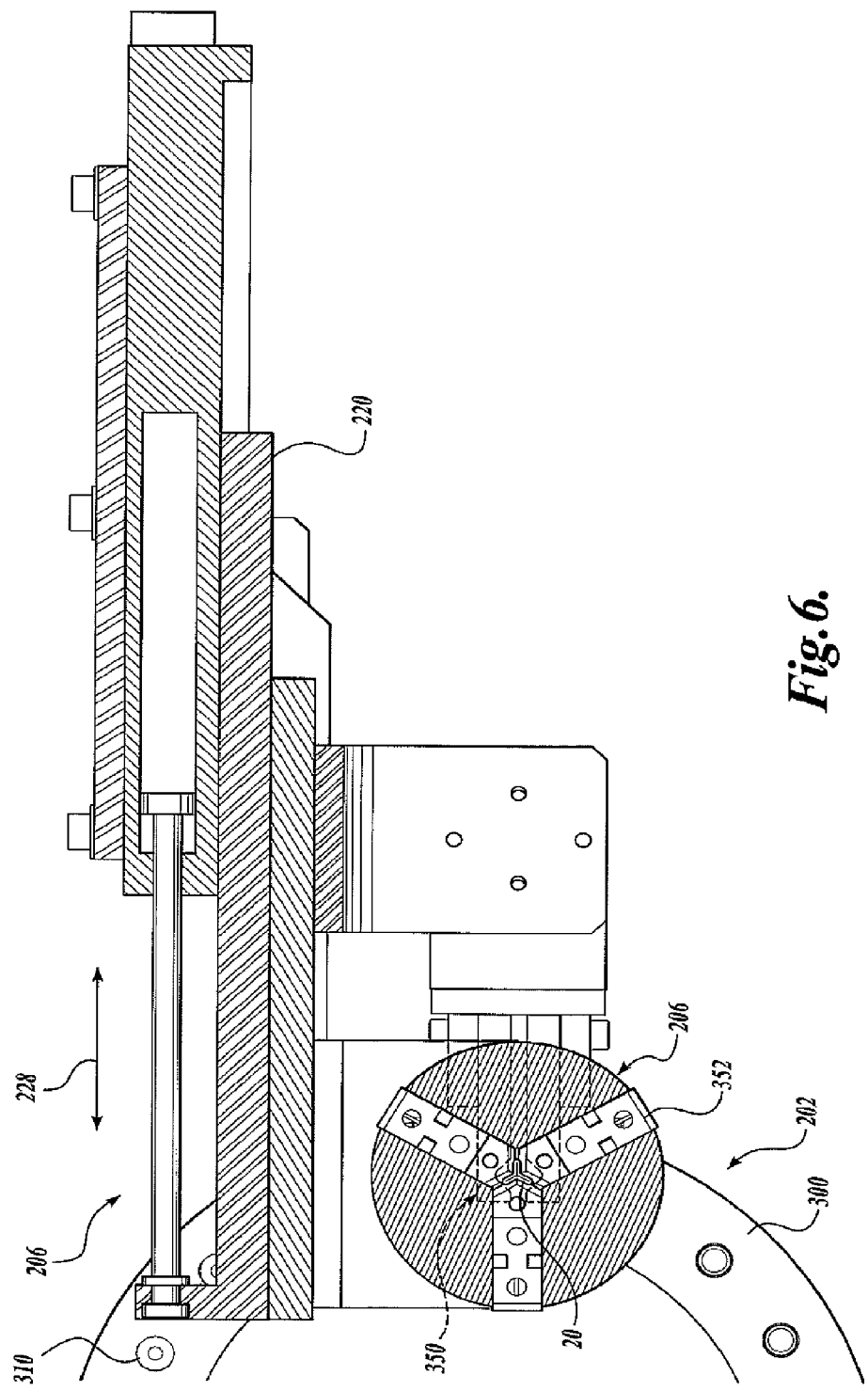
FIG. 6 is a top planar view of the end seal formation assembly of FIG. 4 with portions removed for clarity and showing a jaw clamp forming the end seal of FIG. 2.

As may be best seen by referring to FIGS. 4-6, the carousel 202 moves the seed 20 into proximity to the clamp assembly 206. The clamp assembly 206 includes a seed clamp 350 and an end seal clamp 352. The seed clamp 350 is a well-known clamp, such as one manufactured and sold by PHD, Inc., of 9009 Clubridge Drive, Fort Wayne, Ind. 46809, Part number 19080-2-0001. Any three-jaw end seat clamp 352, such as Part number MHS3-40D1, manufactured and sold by SMC Corp. of America of 3011 N. Franklin Road, Indianapolis, Ind. 46226, is suitable for use with the end seal formation assembly 200 of the present disclosure. Such an end seal clamp 352 may included the option of being heated to assist in the formation of the dead end seal 120.

In operation, the clamp assembly 206 is position along the slide 220 such that it is located near the carousel 202. In this position, the jaws of the seed clamp 350 clamp onto one seed 20 as seen best in FIG. 5. As seen best by referring to FIG. 6, the three jaws of the end seal clamp 352 apply a sealing force to the seed 20 for approximately 3-4 seconds to form the dead end seal 120, as described above. The riser 222 then lifts the seed 20 out of the cavity 310 and the entire clamp assembly 206 is moved by the slide 220 to position the seed 20 above the storage bin 226. In this position, the clamp assembly 200 releases the seed 20 into the storage bin 226 where it is taken for further processing, such as planting.

Although described in the above sequence, the method of forming the dead end seal 120 is not intended to be so limited. As a non-limiting example, the end seal clamp 352 need not apply its clamping force while the seed 20 is located within the cavity 310. Instead, the end seal clamp 352 may apply its clamping force while the seed 20 is in transit to the storage bin 226. As such, additional operational sequences are within the scope of the present disclosure.

While the preferred embodiment of the invention has been illustrated and described, it will be appreciated that various changes can be made therein without departing from the spirit and scope of the invention. As a non-limiting example, the end seal may include more, such as four, five, etc., closure axes. Such examples are also within the scope of the appended claims.

The embodiments of the invention in which an exclusive property or privilege is claimed are defined as follows:

1. An artificial seed, comprising:
   (a) a seed shell having a live end, a dead end and a perimeter;
   (b) a nutritive media disposed within the seed shell;
   (c) a restraint disposed within the seed shell and having a cavity housing an embryo;
   (d) a primary end seal attached to the live end of the seed shell; and
   (e) an end seal disposed on the dead end of the seed shell, the end seal having at least three closure axes forming a seal in a direction extending along each one of the closure axes, wherein the at least three closure axes are located in a plane substantially normal to a longitudinal direction of the seed shell.

2. The artificial seed of claim 1, wherein the at least three closure axes are extending at an obtuse angle to each other.

3. The artificial seed of claim 1, wherein the end seal defines an outer boundary diameter that is no greater than the perimeter of the seed shell.

4. The artificial seed of claim 1, wherein the end seal includes a substantially Y-shaped cross-section.

5. An artificial seed, comprising:
   (a) a seed shell having a live end, a dead end and a perimeter;
   (b) a nutritive media disposed within the seed shell;
   (c) a restraint disposed within the seed shell and having a cavity housing an embryo;
   (d) a primary end seal attached to the live end of the seed shell; and
   (e) an end seal integrally formed with the dead end of the seed shell, the end seal forming a seal along at least three axial directions relative to the seed shell, wherein the at least three axial directions are located in a plane substantially normal to a longitudinal direction of the seed shell.

6. The artificial seed of claim 5, wherein the end seal defines an outer boundary diameter that is no greater than the perimeter of the seed shell.

7. The artificial seed of claim 6, wherein the at least three axial directions are at obtuse angles relative to each other.

8. The artificial seed of claim 5, wherein the at least three axial directions are at obtuse angles relative to each other.

9. The artificial seed of claim 5, wherein the end seal is substantially Y-shaped in cross-section.

* * * * *